United States Patent
Kurose

[11] Patent Number: 5,303,713
[45] Date of Patent: Apr. 19, 1994

[54] BLOOD COLLECTING NEEDLE
[75] Inventor: Katsutoshi Kurose, Yamanashi, Japan
[73] Assignee: Terumo Kabushiki Kaisha, Tokyo, Japan
[21] Appl. No.: 32,998
[22] Filed: Mar. 18, 1993

Related U.S. Application Data
[62] Division of Ser. No. 767,036, Sep. 24, 1991, Pat. No. 5,222,502.

Foreign Application Priority Data
Sep. 26, 1990 [JP] Japan ............................ 2-256390
Nov. 26, 1990 [JP] Japan ............................ 2-321490

[51] Int. Cl.$^5$ .................................................. A61B 5/00
[52] U.S. Cl. ................................. 128/763; 128/771
[58] Field of Search .................. 128/760, 763–766, 128/771

[56] References Cited
U.S. PATENT DOCUMENTS
3,648,684 3/1972 Barnwell et al. .
3,886,930 6/1975 Ryan .
4,416,290 11/1983 Lutkowski ........................ 128/764
4,416,291 11/1983 Kaufman ........................... 128/766
4,679,571 7/1987 Frankel et al. ................... 128/764

FOREIGN PATENT DOCUMENTS
0190558 1/1986 European Pat. Off. .
2-21809 5/1990 Japan .
1345979 2/1974 United Kingdom .

Primary Examiner—Max Hindenburg
Attorney, Agent, or Firm—Frishauf, Holtz, Goodman & Woodward

[57] ABSTRACT

A blood collecting needle of the present invention comprises a hollow cannula, both ends of which are sharp tips, and a hub for supporting the center portion thereof. The hub comprises a sheath which surrounds the cannula in a liquid sealed state projecting from the back section of the hub, formed of an elastic body fixedly mounted on the hub, and an air passage connecting the space between the sheath and the cannula with outside air.

As a result, flashback can be reliably confirmed, for example, when the tip of the cannula pierces an intravenous vein.

14 Claims, 8 Drawing Sheets

BLOOD COLLECTING NEEDLE

This is a division of application Ser. No. 07/767,036 filed Sep. 24, 1991, U.S. Pat. No. 5,222,502.

BACKGROUND OF THE INVENTION

The present invention relates to a blood collecting needle, and more particularly, to a blood collecting needle which is capable of making one or more blood collections after a being for blood collection is connected to a storage chamber which has previously been placed at a negative pressure.

Figure 5:
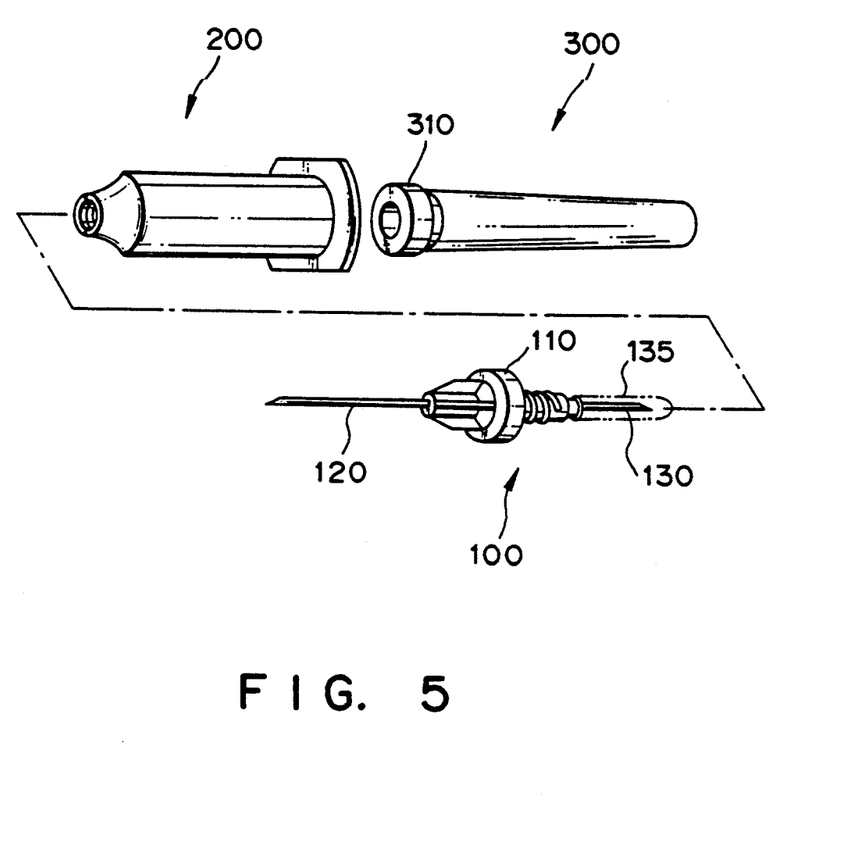
FIG. 5 is an exploded perspective view of a blood collection unit.

In the prior art, blood collecting units by which a plurality of blood collections are made possible with one piercing are frequently used when performing clinical tests. These units, for example, as shown in FIG. 5, comprise cannulas 120 and 130 disposed at both ends of a hub 110, a blood collecting needle 100 having an elastic sheath 135 mounted so as to surround the cannula 130, a cylindrical holder 200 in which the blood collecting needle 100 is fixedly mounted, and a blood collecting tube 300 which is inserted into this holder 200 and placed at a negative pressure (evacuated pressure) beforehand. A rubber or a gass-barrier stopper is inserted into the blood collecting tube 300 so that the inside thereof is maintained at a negative pressure. When collecting blood, first a holder 200 and a blood collecting needle 100 are assembled into one piece. A cannula 120 is made to pierce an intravenous vein and the intravenous vein is secured. The blood collecting tube 300 is pushed into the holder, and the cannula 130 is caused to pass through the elastic sheath 135 and the rubber stopper 310. As a result, blood collection is started and completed in a state in which the pressure inside the blood collecting tube 300 is balanced with the intravenous pressure.

However, in such a conventional vacuum blood collecting system, it is impossible to confirm a so-called flashback, since there is no place where any gas inside the cannula or the elastic sheath can escape when an intravenous vein is pierced and before the blood collecting tube 300 is pushed into the holder. For this reason, there is a danger that blood collection will sometimes start when the cannula pierces at a position other than the intravenous vein.

To solve such a problem, a needle assembly equipped with a mechanism capable of confirming this flashback is proposed in Japanese Patent Publication for Opposition (KOKOKU) No. 2-21809 (Priority of U.S. patent application Ser. No. 645,893, filed on Aug. 31, 1984, now U.S. Pat. No. 4,679,571).

However, the needle assembly proposed therein is very complex in construction, as it comprises a venting apparatus as a communicating path disposed inside the hub, ring-like compressed sleeves which are inserted into a communicating path disposed inside the apparatus and has drawbacks, such as swelling due to water content, etc. This presents a problem in that it cannot be mass-produced inexpensively. In the needle of the present invention, a negative pressure is applied to sleeves housed inside the housing at the time blood is collected. The needle cannot be fully sealed from the outside, lacks adequate safety precautions, and has a lot of dead volume.

SUMMARY OF THE INVENTION

The present invention has been devised to solve the above-mentioned problems of the prior art. An object of the present invention is to provide a blood collecting needle having a very simple construction and a mechanism capable of reliably confirming flashback.

To this end, according to the present invention, there is provided a blood collecting needle, comprising: a hollow cannula, both ends of which are sharp tips; and a hub for supporting substantially the center portion thereof, wherein the hub further comprises a sheath which surrounds the cannula in a liquid sealed state projecting from the back section of the hub, formed of an elastic body fixedly mounted on the hub, and an air passage connecting the space between the sheath and the cannula with outside air.

In addition, another object of the present invention is to provide a blood collecting needle in which impurities from the outside will not enter, and the blood specimen inside will not leak outside.

To this end, according to the present invention, there is provided a blood collecting needle comprising a substantially cylindrical hub; a cannula extending from both ends of the hub in an axial direction and having sharp tips whose internal path is continuous; and a cylindrical elastic sheath with a bottom, fitted into the hub in a liquid sealed state in such a manner as to surround one of the extending ends of the cannula, wherein the hub comprises an axial communicating passage into which the cannula is inserted and fixed, an air passage connecting the internal cavity of the cylindrical elastic sheath having a bottom with the outside atmosphere, and a permeable filter, fixedly mounted on the outside mouth section of the air passage, having a small hole for permitting gases but not liquids to pass.

Other features and advantages of the present invention will be apparent from the following description taken in conjunction with the accompanying drawings, in which like reference characters designate the same or similar parts throughout the figures thereof.

DETAILED DESCRIPTION OF THE PREFERRED EMBODIMENTS

A first embodiment of a blood collecting needle of the present invention will now be explained with reference to FIG. 1.

Figure 1:
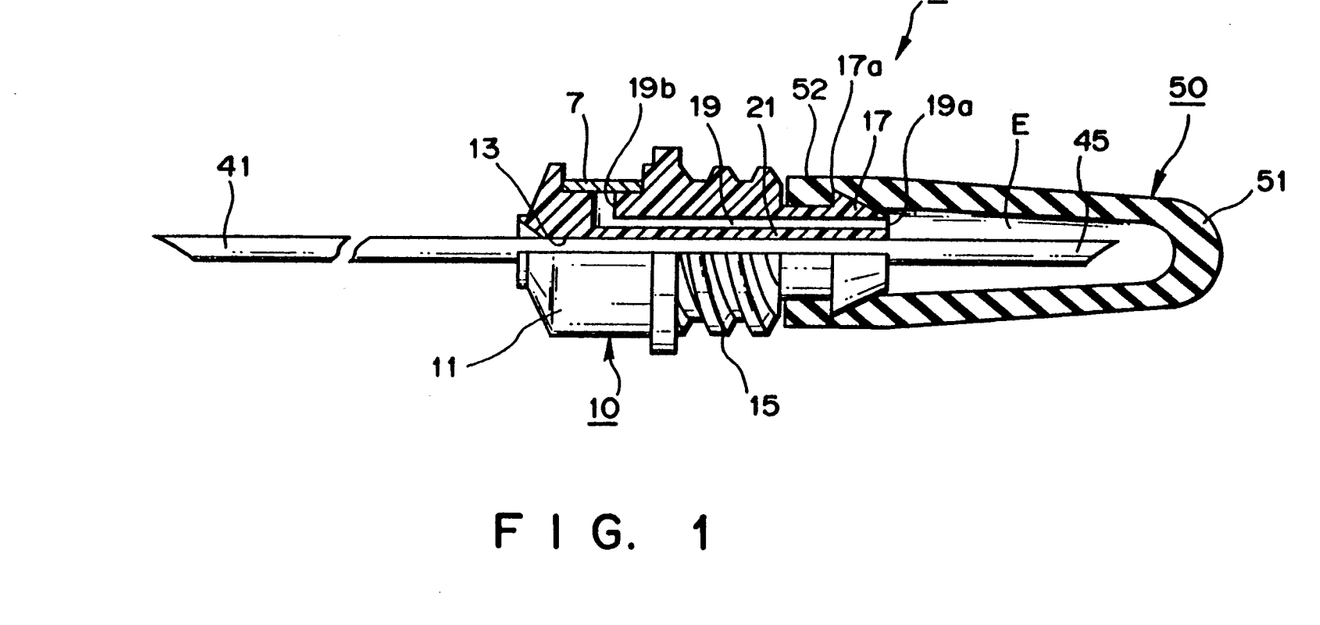
FIG. 1 is a partially sectional view of a blood collecting needle according to a first embodiment of the present invention.

As shown in FIG. 1, a blood collecting needle 1 of the present invention comprises a substantially cylindrical hub 10, cannulas 41 and 45 extending from both ends of the hub 10 in an axial direction and having sharp tips whose internal path is continuous, and a cylindrical elastic sheath 50 having a bottom fitted into the hub 10 in a liquid sealed state in such a manner as to surround one of the extending ends of the cannula 45.

The hub 10 is formed in a substantially cylindrical shape. Disposed in the inside thereof are a communicating cavity 13 which is positioned through the center in an axial direction thereof and an air passage 19 connecting the internal cavity section E of the cylindrical elastic sheath 50 having a bottom with the outside atmosphere.

The communicating passage 13 is a hole into which cannulas 41 and 45 are inserted and fixed. The inner diameter thereof is slightly larger than the outer diameter of the cannulas 41 and 45. Usually, the difference between them is approximately 0 to 0.3 mm.

In the air passage 19, an end 19a thereof is positioned at a back end of the hub 10 and disposed in such a manner as to connect with the internal cavity E of the elastic sheath 50. The other end 19b of the air passage 19 is disposed, for example, on the outer surface of the trunk section of the hub 10 so as to communicate with the outside atmosphere. In this embodiment, the air passage 19 is shaped in the letter L in such a way that it is axially bored a predetermined length from the one end 19a spaced by a given partition wall 21 from the axial communicating passage 13, and then the direction of the passage 19 is changed toward the outer surface and bored to the outside.

Although, in this embodiment, the cross section of the air passage 19 is shaped in a circle, it is not limited to this shape, but various shapes may be used. The diameter of the air passage 19 is approximately 0.2 to 2 mm.

An air permeable filter 7 is fused by ultra-sonic fusion, thermal fusion or the like on the other end 19b of such an air passage 19, such other end 19b connecting with the outside atmosphere. This air permeable filter 7 has a small passage for permitting gases but not liquids to pass. This filter should preferably have a water repellent property. In this embodiment, fluorine type resin, such as teflon, or olefin type resin, such as PP, PE or the like, is contained therein.

Further, in the hub 10, a screw section 15 is provided on the outer surface in the center portion of the trunk section of the main body thereof. The mouth section of the holder 200 (see FIGS. 3 and 4), which is equal to one blood collection unit, is screwed to the screw section 15. Furthermore, a locking section 17 for locking the elastic sheath 50 is formed in the back end of the hub 10. The shape of the locking section 17 is not particularly limited, but preferably is shaped in such a way that the elastic sheath 50 cannot be easily released. In this embodiment, as an example, the locking section 17 has a locking projection 17a projecting in the form of a jaw.

The elastic sheath 50 locked to such an engagement section is cylindrically shaped and has a bottom section 51. It has an internal cavity section E serving as a space surrounding one extending end of the cannulas 45. It is required that this elastic sheath 50 have a proper elasticity such that the elastic sheath 50 can be sealed again after it is pierced temporarily by the cannula 45 during blood collection. As materials to be used, synthetic rubber, elastomer, etc. can be employed. In particular, materials having transparent or semi-transparent characteristics should preferably be used so as to confirm a flashback phenomenon such that blood is jetted out when the cannula 41 is made to pierce an intravenous vein. The dimensions of such an elastic sheath are usually approximately 10 to 30 mm in length with an outer diameter of 1 to 3 mm.

When a specimen is being collected, the sharp tips of the cannulas 41 and 45 inserted into the communicating passage 13 of the hub 10 are respectively made to pierce one specimen source, such as blood inside an intravenous vein, or a specimen storage chamber, such as a so-called vacuum or negative-pressure blood collection tube or the like. The cannulas 41 and 45 may be separate bodies, or may be continuous and made into one piece. Such cannulas 41 and 45 are fixedly mounted by various kinds of bonding agents in a state in which they are inserted into the communicating passage 13. The hub 10 is usually formed by injection molding. To make flashback easily confirmed, transparent or semi-transparent materials are preferable. To be specific, the following can be employed: polypropylene, polyethlene, polystyrene, polyethylene terephthalate, polymethyl pentene, polycarbonate, polyacrylonitrile, resin materials of ABS, etc. The dimensions of the hub 10 are approximately 10 to 30 mm in length with an outer diameter of 5 to 15 mm.

With the above construction, for example, when the cannula 41 is made to pierce an intravenous vein, a flashback phenomenon can be confirmed since the pressure of the internal cavity section E of the elastic sheath 50 is lower than a blood pressure value inside the intravenous vein. In other words, when the cannula 41 is not made to correctly pierce an intravenous vein, the flashback phenomenon does not occur. Therefore, a wasteful operation of collecting blood need not be performed.

Figure 2:
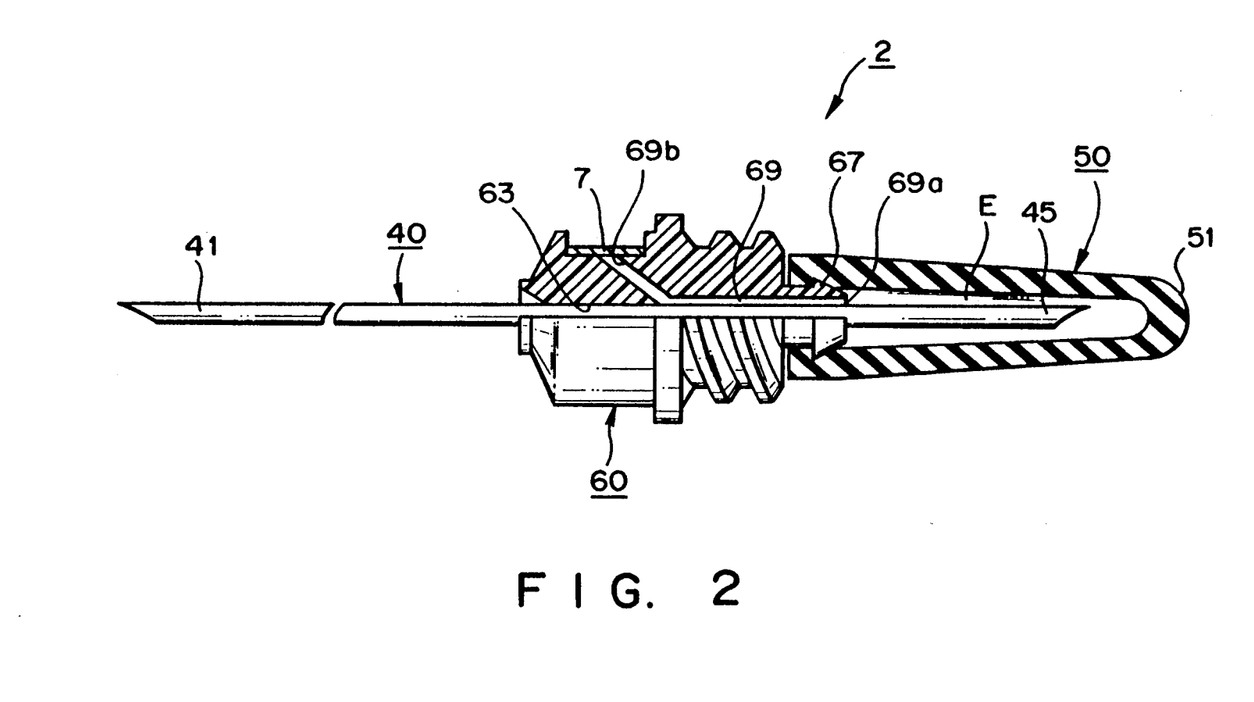
FIG. 2 is a partially sectional view of a blood collecting needle according to a second embodiment of the present invention.

Next, a second embodiment of a blood collecting needle of the embodiment will be explained with reference to FIG. 2.

A point of fundamental difference between a blood collecting needle 2 of the second embodiment and that of the first embodiment is the construction of an air passage disposed inside the hub. That is, as regards an air passage 69 of the second embodiment, portions thereof, in particular, portions oriented in an axial direction, are formed to be in contact with an axial communicating passage 63. As a consequence, a part of the outer surface of a cannula constitutes a part of the air passage 69 when the cannula is inserted into the communicating passage 63.

With such a construction, it is possible to make small the outer diameter of the locking section 67 for locking the elastic sheath 50, and a communicating passage can be easily formed by injection molding.

A third embodiment of a blood collecting needle will be explained with reference to FIGS. 6 and 7.

Figure 7:
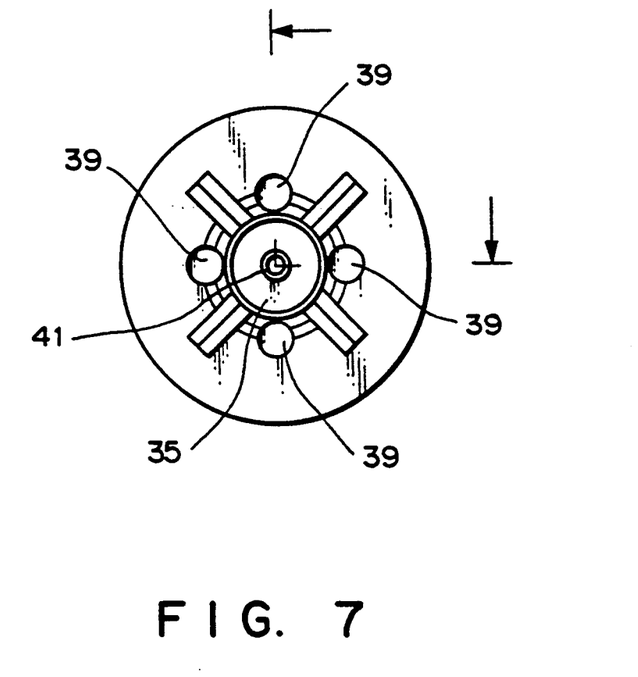
FIG. 7 is a front view of the blood collecting needle the third embodiment.

FIG. 7 is a front view of the blood collecting needle of the present embodiment. As shown in FIG. 7, four holes 39 are provided on the hub 10 around the axis of the cannula 41.

Figure 6:
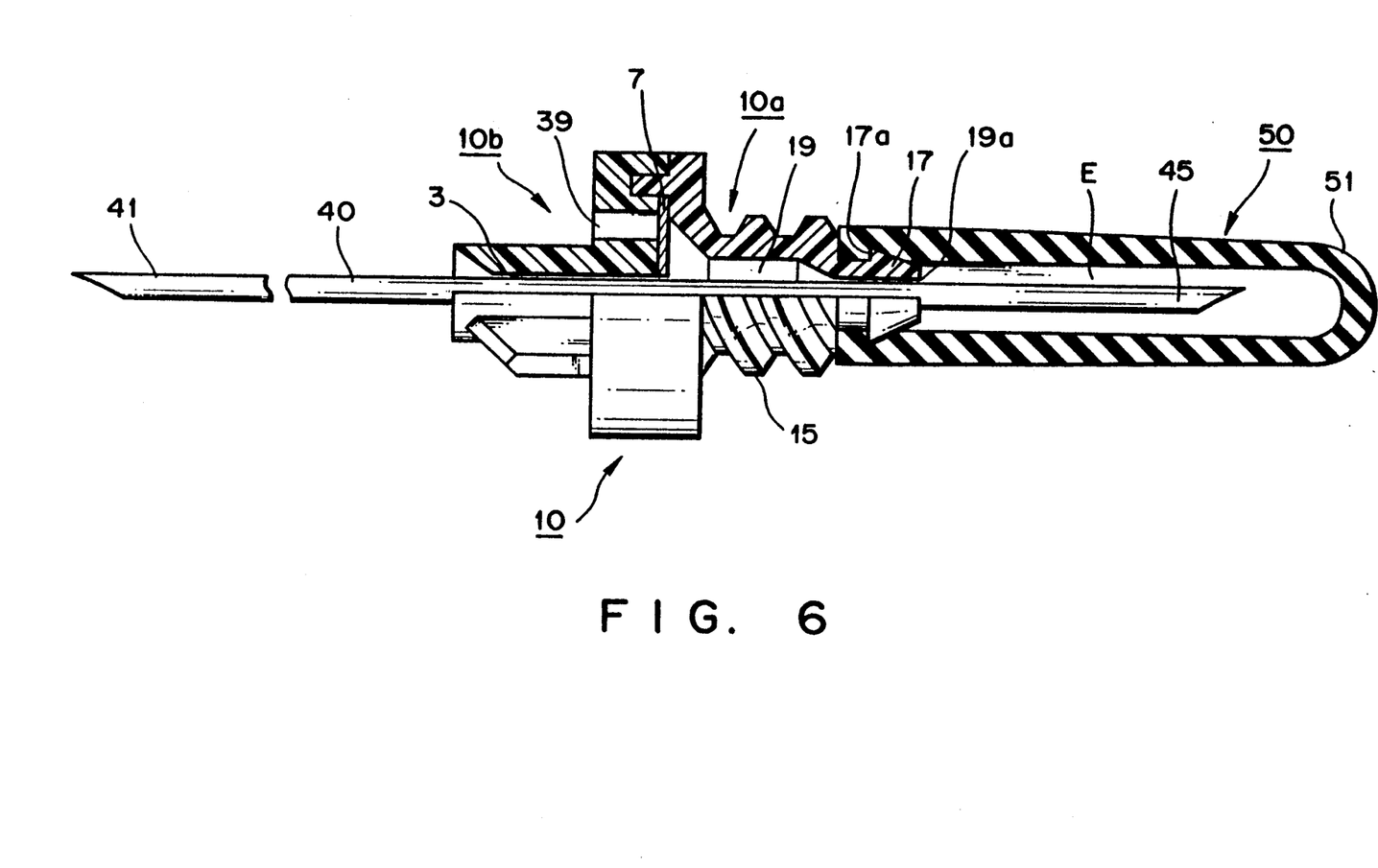
FIG. 6 is a partially sectional view of a blood collecting needle according to a third embodiment of the present invention.

FIG. 6 is a partially sectional view of the blood collecting needle of the present embodiment. As shown, the hub 10 of the present third embodiment comprises of two members 10a,10b. The members 10a,10b and filter 7 are fixed to each other by ultra-sonic fusion, thermal fusion or other well known well known methods. Also as shown, the cannula 40 is inserted into the hub 10 and fixed thereto with an adhesive S.

According to the third embodiment, the hub 10 is manufactured easily and it is possible to reduce the cost for the manufacture.

A fourth embodiment of the blood collecting needle will be explained with reference to FIGS. 8 and 9.

According to above described embodiments, it is possible to confirm the flashback. However, there is a fear that the blood leaks from the filter 7 by the cause high pressure against the filter 7 if the air in the hub 10 was very little. To secure air in the hub 10, the present fourth embodiment provides the structure of the needle as shown FIG. 8.

Figure 8:
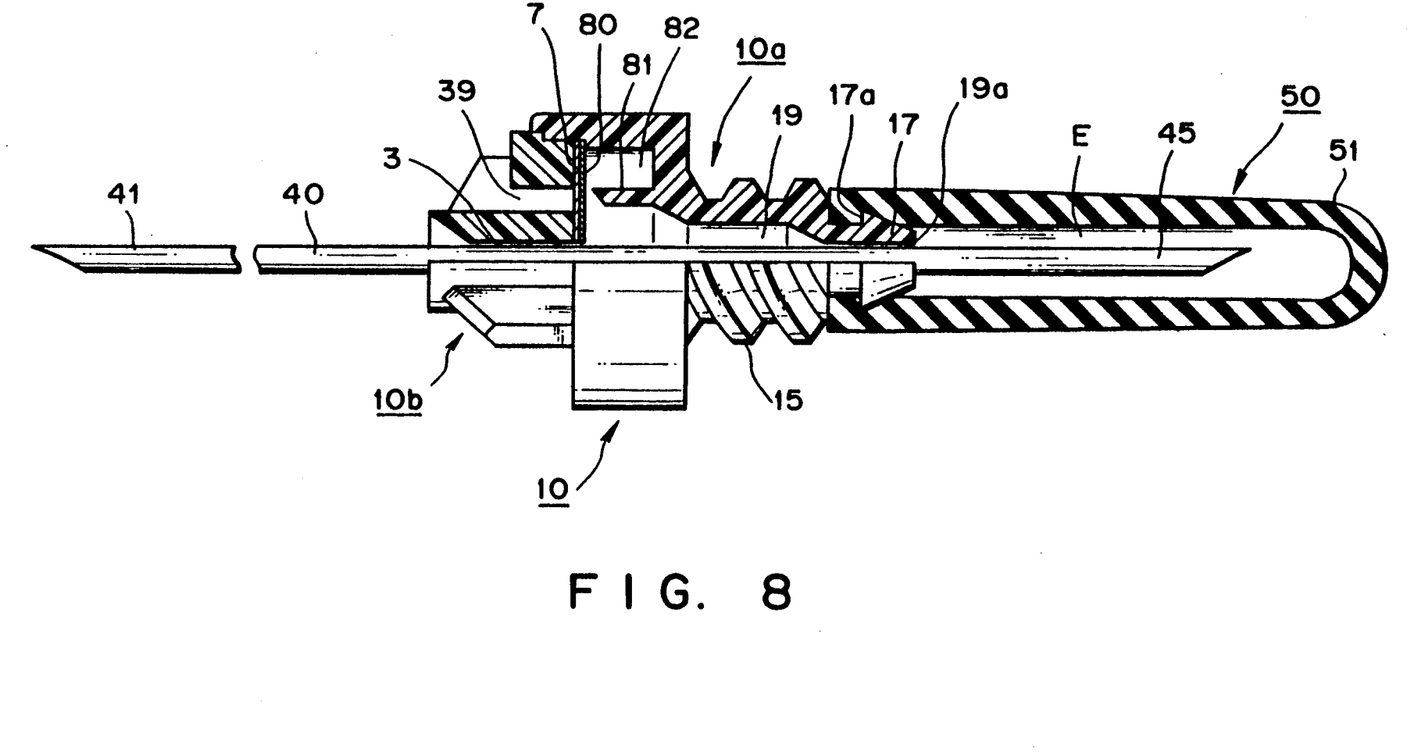
FIG. 8 is a partially sectional view of a blood collecting needle according to a fourth embodiment of the present invention.

The difference between the present embodiment and the above described embodiments is to provide the air chamber in the neighborhood of the outer portion of the air passage 19 which is contacted by the filter 7 as shown in FIG. 8. It is noted that four holes 39 are provided on the hub 10b around the cannula 41 in the same manner as the third embodiment.

Figure 9:
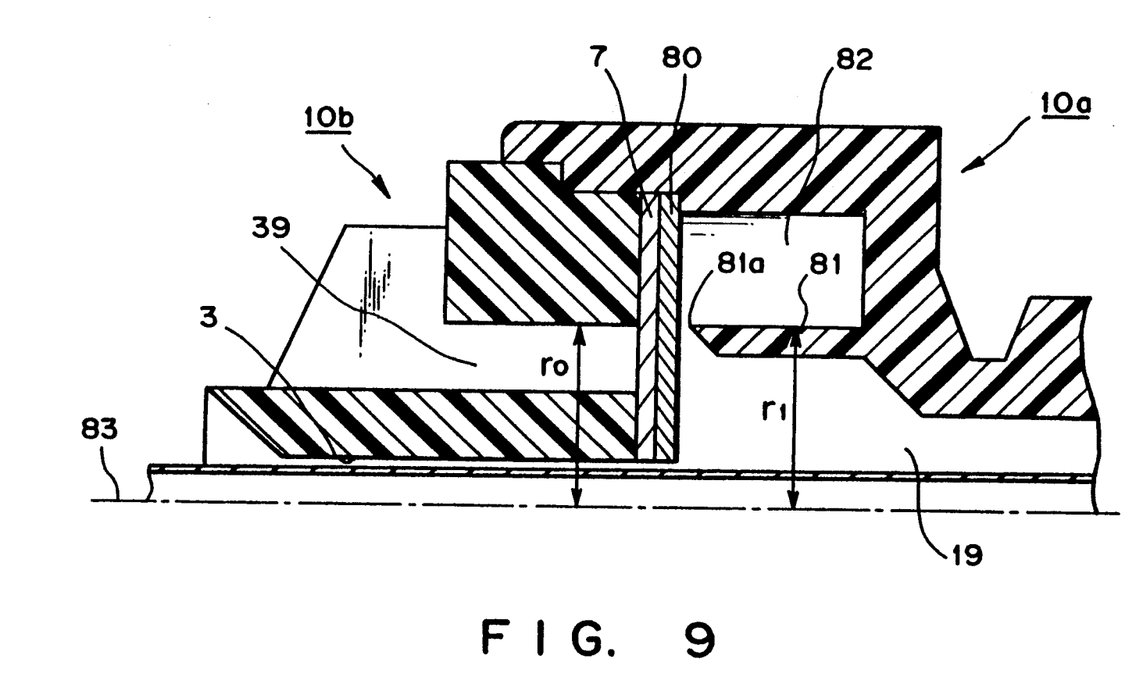
FIG. 9 is a magnified section around the filter of the fourth embodiment.

FIG. 9 shows a magnified section view around the filter 7. In the fourth embodiment, the filter 7 is reinforced by the reinforcement member 80 which prevents the filter 7 from bending.

In this embodiment, the blood that flows in the air passage 19 does not enter into the air chamber 82 but flows through the filter 7 and reinforcement member 80 When the blood passed through the filter 7 and reinforcement member 80, the filter 7 becomes wet, air flow through the filter 7 is prevented, thus much of air remains in the air chamber 82. The air in the air chamber 82 acts as a cushion and prevents blood from leaking through the filter 7. The end of portion 81a of the chamber wall 81 is tapered in such a manner that it is closer to the filter 7 than the opposite edge. The tapering is to facilitate damp throughout of the filter 7.

In the FIG. 9, the radius $r_1$ of the air chamber 82 is made to be substantially equal to the radius $r_0$ of the hole 39. However, it is preferable to structure the device so that the radius $r_1$ is greater than the radius $r_0$. If $r_1$ is less than $r_0$, the blood has a tendency to flow into the air chamber 82, thus making the volume of air chamber 82 smaller.

As explained above, according to the present embodiment, because air can be retained in the hub 10, blood will not leak through the filter 7.

The filter 7 of embodiments 1 to 4 is made from porous material which has many micro-holes. The micro-hole is preferably between 0.2 $\mu m$ and 10 $\mu m$. In the embodiments, the polytetrafluoroethylene which has micro holes of 1 $\mu m$ to 3 82 m diameter is used. Also, the thickness of the filter 7 is preferably between 0.05 mm and 0.5 mm, determined by the air flow resistance. In the present embodiments, a thickness between 0.07 mm to 0.16 mm is used. The reinforcement member 80 is formed of a hydrophilic member of the surface of the member which is hydrophilic-treated. For example, a surface of which polyester (200 mesh) is plasma treated is use for the reinforcement member 80.

Figure 3:
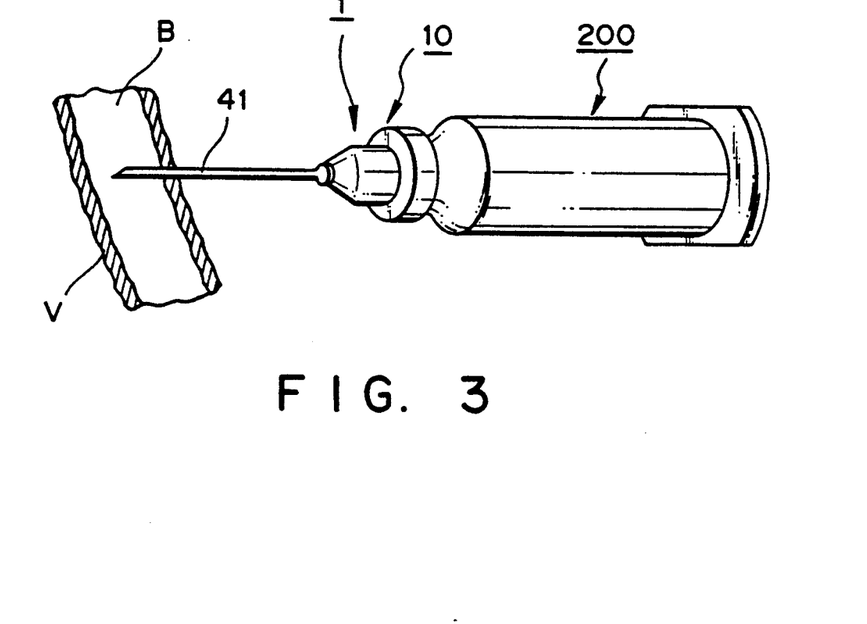
FIG. 3 is a schematic view showing an operation of a blood collecting needle of the present invention.

Next, an explanation will be provided of the operation of the above-described first to fourth blood collecting needles. As shown in FIG. 3, a mouth section of the holder 200 is screwed to the screw section 15 provided on the outer surface of the hub 10 of the blood collecting needle 1, and the blood collecting needle and the holder 200 are made into one piece. In this state, the first cannula 41, which is a blood collecting needle, is made to pierce a blood vessel V. Thereupon, the blood inside the blood vessel V flows into the internal cavity section E of an elastic sheath after passing from the internal passage of the cannula 41 to the internal passage of the cannula 45. The blood further rises to the inside of the air passage and stops at the air permeable filter 7. As the result of at least one of either the hub 10 or the elastic sheath 50 being formed of a transparent or semi-transparent material, flashback can be confirmed easily.

Figure 4:
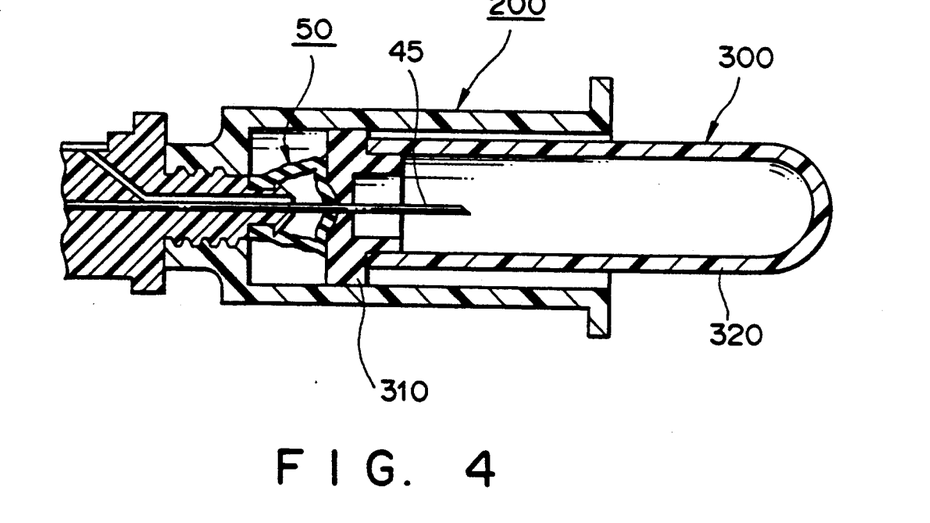
FIG. 4 is a cross-sectional view showing a state during blood collection.

When this flashback is confirmed, since at least the tip of the cannula 41 is positioned inside an object intravenous vein, the blood collecting tube 300 is pushed thereinto from the opening of the back end of the holder 200. This state is shown in FIG. 4. As a result, the cannula 45 passes through the elastic sheath 50 and the rubber stopper of the blood collecting tube 300, and the tip thereof reaches the inside of the blood vessel to be collected. Since the pressure inside the blood collecting tube 300 is fully smaller than the blood pressure in the intravenous vein, the blood continues to flow thereinto until the difference between these pressures reaches a predetermined value.

When the inventor of the present invention made an experiment for confirming flashback, flashback was confirmed even under an intravenous pressure as low as approximately 5 cmaq. That is, the blood collecting needle of the present invention has an advantage in that it is capable of reliably confirming flashback with a very simple construction.

As has been explained above, according to the first invention, it is possible to provide a blood collecting needle having a very simple construction and capable of reliably confirming flashback.

According to the second invention, it is possible to provide a blood collecting needle in which impurities from the outside will not enter, and the blood specimen inside will not leak outside.

As many apparently widely different embodiments of the present invention can be made without departing from the spirit and scope thereof, it is to be understood that this invention is not limited to the specific embodiments thereof except as defined in the appended claims.

What is claimed is:

1. A blood collecting needle, comprising:
   a hollow cannula, having opposite ends, both opposite ends having pointed tips; and
   a hub for holding a substantially center portion of the cannula;
   said hub comprising:
   a sheath which surrounds a portion of one end of the cannula in a liquid sealed state, and which projects from a back section of the hub, the sheath being formed of an elastic body fixedly mounted on the hub;
   means for defining an air passage connecting a space between the sheath and the cannula with outside air, said air passage being provided outside of said cannula; and
   a filter arranged at an end portion of the air passage, and said filter having small holes for permitting gases but not liquids to pass therethrough at said end portion of the air passage; and
   wherein at least one of said hub and said sheath is formed of one of a transparent and semi-transparent material.

2. The blood collecting needle of claim 1, wherein:
the hub comprises two members coupled together;
the filter is fixed between the two members; and
at least one of the two members defining a cavity for forming the air passage, said at least one member including means for mounting the sheath thereto, the cavity having at least a diameter larger than an outside diameter of the cannula.

3. The blood collecting needle of claim 1, wherein the filter contains fluorine type resin.

4. The blood collecting needle of claim 1, wherein the filter contains olefin type resin.

5. A blood collecting needle, comprising:
a cannula having opposite ends, both opposite ends having pointed tips; and
a hub having a cavity formed therein for holding a substantially center portion of the cannula; and
a cylindrical elastic sheath having a bottom portion fitted to the hub in a liquid sealed state in such a manner as to surround one end portion of the cannula;
said hub comprising:
means for defining at least one air passage which connects a space between the sheath and the cannula with outside air, said air passage being provided outside of said cannula, each of the at least one air passages having a filter arranged at an end portion thereof, said filter having small holes for permitting gases but not liquids to pass therethrough; and
wherein at least one of said hub and said sheath is formed of one of a transparent and semi-transparent material.

6. The blood collecting needle of claim 5, wherein:
the hub comprises two members coupled together;
the filter is fixed between the two members; and
at least one of the two members defining a cavity for forming the air passage, said at least one member including means for mounting the sheath thereto, the cavity having at least a diameter larger than an outside diameter of the cannula.

7. The blood collecting needle of claim 5, wherein the filter contains fluorine type resin.

8. The blood collecting needle of claim 5, wherein the filter contains olefin type resin.

9. A blood collecting needle, comprising:
a hollow cannula, having opposite ends, both opposite ends having pointed tips; and
a hub for holding a substantially center portion of the cannula;
said hub comprising:
a sheath which surrounds a portion of one end of the cannula in a liquid sealed state, and which projects from a back section of the hub, the sheath being formed of an elastic body fixedly mounted on the hub;
means for defining an air passage connecting a space between the sheath and the cannula with outside air; and
a filter arranged at an end portion of the air passage, said filter being coupled to said means for defining an air passage, and said filter having small holes for permitting gases but not liquids to pass therethrough at said end portion of the air passage; and
wherein:
the hub comprises two members coupled together;
the filter is fixed between the two members; and
at least one of the two members defining a cavity for forming the air passage, said at least one member including means for mounting the sheath thereto, the cavity having at least a diameter larger than an outside diameter of the cannula.

10. The blood collecting needle of claim 9, wherein the sheath is formed of a transparent material.

11. The blood collecting needle of claim 9, wherein the sheath is formed of a semi-transparent material.

12. A blood collecting needle, comprising:
a cannula having opposite ends, both opposite ends having pointed tips; and
a hub having a cavity formed therein for holding a substantially center portion of the cannula; and
a cylindrical elastic sheath having a bottom portion fitted to the hub in a liquid sealed state in such a manner as to surround one end potion of the cannula;
said hub comprising:
means for defining at least one air passage which connects a space between the sheath and the cannula with outside air, each of the at least one air passages having a filter arranged at an end portion thereof, said filter having small holes for permitting gases but not liquids to pass therethrough; and
wherein
the hub comprises two members coupled together;
the filter is fixed between the two members; and
at least one of the two members defining a cavity for forming the air passage, said at least one member including means for mounting the sheath thereto, the cavity having at least a diameter larger than an outside diameter of the cannula.

13. The blood collecting needle of claim 12, wherein the sheath is formed of a transparent material.

14. The blood collecting needle of claim 12, wherein the sheath is formed of a semi-transparent material.

* * * * *

UNITED STATES PATENT AND TRADEMARK OFFICE
CERTIFICATE OF CORRECTION

PATENT NO. : 5,303,713

DATED : April 19, 1994

INVENTOR(S) : KUROSE, Katsutoshi

It is certified that error appears in the above-identified patent and that said Letters Patent is hereby corrected as shown below:

The title page, showing the illustrative figure, should be deleted and substitute therefor the attached title page.

Add the Drawing Sheets, consisting of Figs. 6,8 & 9 as shown on the attached pages.

Column 5, line 55, "82 m" should be --$\mu$m--.

Signed and Sealed this

Fourth Day of July, 1995

Attest:

BRUCE LEHMAN

Attesting Officer

Commissioner of Patents and Trademarks

United States Patent [19]

Kurose

[11] Patent Number: 5,303,713
[45] Date of Patent: Apr. 19, 1994

[54] BLOOD COLLECTING NEEDLE

[75] Inventor: Katsutoshi Kurose, Yamanashi, Japan

[73] Assignee: Terumo Kabushiki Kaisha, Tokyo, Japan

[21] Appl. No.: 32,998

[22] Filed: Mar. 18, 1993

Related U.S. Application Data

[62] Division of Ser. No. 767,036, Sep. 24, 1991, Pat. No. 5,222,502.

[30] Foreign Application Priority Data

Sep. 26, 1990 [JP] Japan .................................. 2-256390
Nov. 26, 1990 [JP] Japan .................................. 2-321490

[51] Int. Cl.⁵ .................................................. A61B 5/00
[52] U.S. Cl. .................................... 128/763; 128/771
[58] Field of Search ................... 128/760, 763-766, 128/771

[56] References Cited

U.S. PATENT DOCUMENTS 3,648,684  3/1972  Barnwell et al.
3,886,930  6/1975  Ryan
4,416,290  11/1983  Lutkowski .................... 128/764
4,416,291  11/1983  Kaufman ...................... 128/766
4,679,571  7/1987  Frankel et al. ............... 128/764

FOREIGN PATENT DOCUMENTS 0190558  1/1986  European Pat. Off.
2-21809   5/1990  Japan.
1345979   2/1974  United Kingdom.

Primary Examiner—Max Hindenburg
Attorney, Agent, or Firm—Frishauf, Holtz, Goodman & Woodward

[57] ABSTRACT

A blood collecting needle of the present invention comprises a hollow cannula, both ends of which are sharp tips, and a hub for supporting the center portion thereof. The hub comprises a sheath which surrounds the cannula in a liquid sealed state projecting from the back section of the hub, formed of an elastic body fixedly mounted on the hub, and an air passage connecting the space between the sheath and the cannula with outside air.

As a result, flashback can be reliably confirmed, for example, when the tip of the cannula pierces an intravenous vein.

14 Claims, 8 Drawing Sheets

UNITED STATES PATENT AND TRADEMARK OFFICE
CERTIFICATE OF CORRECTION

PATENT NO. : 5,303,713
DATED : April 19, 1994
INVENTOR(S) : Kurose, Katsutoshi

It is certified that error appears in the above-indentified patent and that said Letters Patent is hereby corrected as shown below:

FIG. 6

UNITED STATES PATENT AND TRADEMARK OFFICE
CERTIFICATE OF CORRECTION

PATENT NO. : 5,303,713
DATED : April 19, 1994
INVENTOR(S) : Kurose, Katsutoshi

It is certified that error appears in the above-indentified patent and that said Letters Patent is hereby corrected as shown below:

FIG. 8

UNITED STATES PATENT AND TRADEMARK OFFICE
CERTIFICATE OF CORRECTION

PATENT NO. : 5,303,713
DATED : April 19, 1994
INVENTOR(S) : Kurose, Katsutoshi

It is certified that error appears in the above-indentified patent and that said Letters Patent is hereby corrected as shown below:

FIG. 9